United States Patent
Bertrand et al.

(10) Patent No.: US 7,312,331 B2
(45) Date of Patent: Dec. 25, 2007

(54) STABLE CYCLIC (ALKYL)(AMINO) CARBENES AS LIGANDS FOR TRANSITION METAL CATALYSTS

(75) Inventors: Guy Bertrand, Riverside, CA (US); Vincent Lavallo, Riverside, CA (US); Yves Canac, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/449,568

(22) Filed: Jun. 7, 2006

(65) Prior Publication Data

US 2007/0004917 A1    Jan. 4, 2007

Related U.S. Application Data

(60) Provisional application No. 60/691,572, filed on Jun. 17, 2005.

(51) Int. Cl.
*C07F 15/00* (2006.01)
*C07F 7/02* (2006.01)
*C07C 209/00* (2006.01)

(52) U.S. Cl. ............... 546/2; 546/14; 546/184; 548/400; 548/402; 564/395; 568/316; 585/400

(58) Field of Classification Search ............ 546/2, 546/14, 182, 184; 548/400, 402; 564/395; 568/315, 316; 585/400
See application file for complete search history.

(56) References Cited

U.S. PATENT DOCUMENTS 6,759,537 B2    7/2004  Grubbs et al.

6,888,002 B2    5/2005  Herrmann et al.

OTHER PUBLICATIONS

Littke et al., Angew. chem. Int. Ed., vol. 41, pp. 4176-4211 (2002).*
Lavallo et al., Journal of American Chemical Society, vol. 126, No. 28, pp. 8670-8671 (2004).*
Canac et al., Journal of Organometallic Chemistry, vol. 689, pp. 3857-3865 (2004).*
Lavallo et al. article, Angew. Chem. Int. Ed., vol. 44, pp. 5705-5709 (published online Aug. 1, 2005).*
Littke, A.F. et al. *Angew. Chem. Int. Ed.*, 41, 4176 (2002).
Zapf, A. et al. *Chem. Commun.* 431 (2005).
Miura, M. *Angew. Chem. Int. Ed.*, 43 2201 (2004).
Gstöttmayr, C.W.K et al., *Angew. Chem. Int. Ed.* 41 1363 (2002).
Altenhoff, G. et al., *J. Am. Chem. Soc.* 126 15195 (2004).
Huang, J. et al., *Organometallics* 18, 2370 (1999).
Mayr, M. et al., *Chem. Eur. J.* 10, 1256 (2004).
Kirmse, W. et al., *Angew. Chem. Int. Ed.* 43, 1767 (2004).
Canac, M. et al., *J. Organomet. Chem.* 689, 3857 (2004).
Lavallo, V. et al., *J. Am. Chem. Soc.*, 126, 8670 (2004).
Lavallo, V. et al., *J. Angew. Chem. Int. Ed.* , 44, 5705 (2005).

* cited by examiner

*Primary Examiner*—Porfirio Nazario-Gonzalez
(74) *Attorney, Agent, or Firm*—Townsend and Townsend and Crew LLP

(57) ABSTRACT

Stable carbene ligands are provided having a carbene center flanked by a quaternary carbon and an amino group, and having utility in the preparation of various transition metal complexes.

16 Claims, 2 Drawing Sheets

STABLE CYCLIC (ALKYL)(AMINO) CARBENES AS LIGANDS FOR TRANSITION METAL CATALYSTS

CROSS-REFERENCES TO RELATED APPLICATIONS

This application claims the benefit of Provisional Application Ser. No. 60/691,572, filed Jun. 17, 2005, the content of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The availability of catalysts to perform specific transformations is critical for both industry and academia. Over the years, the success of homogeneous catalysis can be attributed largely to the development of a diverse range of ligand frameworks that have been used to tune the behavior of a variety of metal-containing systems. Advances in ligand design have allowed not only for improvements of known processes in terms of scope, mildness and catalyst loadings, but also for the discovery of new selective reactions. A good illustration is given by palladium-catalyzed coupling reactions, which are applied to a wide area of endeavors ranging from synthetic organic chemistry to materials science (see, A. de Meijere, F. Diederich, Eds., *Metal-Catalyzed Cross-Coupling Reactions* (Wiley-VCH, Weinheim, 2004). E. Negishi, Ed., *Handbook of Organopalladium Chemistry for Organic Synthesis* (Wiley, Hoboken, N.J., 2002)). For these catalytic processes, which represent some of the most powerful and versatile tools available for synthetic chemists, major advances have recently been reported thanks to the use of bulky, electron-rich, phosphines and cyclic diaminocarbenes (NHCs) (see A. F. Littke, G. C. Fu, *Angew. Chem. Int. Ed.* 41, 4176 (2002); A. Zapf, M. Beller, *Chem. Commun.* 431 (2005); and M. Muira, *Angew. Chem. Int. Ed.* 43, 2201 (2004)). These ligands stabilize the active catalytic species, and accelerate the important catalytic steps, namely oxidative addition, transmetallation, and reductive elimination. On the other hand, excessive steric hindrance can present some drawbacks for the coupling of bulky reactants (see, C. W. K. Gstöttmayr, V. P. W. Bohm, E. Herdtweck, M. Grosche, W. A. Herrmann, *Angew. Chem. Int. Ed.* 41, 1363 (2002)). To overcome this problem Glorius has successfully developed ligands with "flexible steric bulk" using the conformational flexibility of cyclohexane (see, G. Altenhoff, R. Goddard, C. W. Lehmann, F. Glorius, *J. Am. Chem. Soc.* 126, 15195 (2004)). Despite the advances in carbene ligand chemistry, there exists a need for ligands which are strong σ-donors, more electron-rich than either the phosphine or diaminocarbene ligand families, yet provide the steric discrimination of the flexible steric bulk ligands. Surprisingly, the present invention addresses these needs.

BRIEF SUMMARY OF THE INVENTION

In one aspect, the present invention provides cyclic alkyl amino carbenes having the formula:

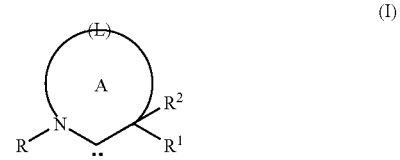

(I)

wherein the A ring is a 4-, 5-, 6- or 7-membered ring; and L is a linking group representing from one to four ring vertices selected from the group consisting of C, O, N, B, Al, P, S and Si with available valences optionally occupied by hydrogen, oxo or $R^a$ substituents. The letter R represents a member selected from $C_{1-10}$ alkyl, $C_{2-10}$ alkenyl, $C_{2-10}$ alkynyl and aryl, wherein each is optionally substituted with $R^a$ substituents, preferably with from one to eight, and more preferably with one to four $R^a$ substituents. The symbols $R^1$ and $R^2$ are each members independently selected from $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl and $C_{1-10}$ alkylsulfinyl, or optionally are combined to form a 3- to 12-membered spirocyclic ring, more preferably a 3- to 7-membered spirocyclic ring, wherein the spirocyclic ring is optionally substituted with $R^b$ substituents, more preferably one to twelve $R^b$ substituents and still more preferably with from one to eight $R^b$ substituents. The optional substituents $R^a$ and $R^b$, in each instance, are independently selected from $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl and $C_{1-10}$ alkylsulfinyl. Still other suitable substituents for $R^a$ and $R^b$ are oxo, amino (including mono- and di-alkylamino and acylamino), imines, nitrogen heterocycles (e.g., pyridines), hydroxy, thiol, thiono, phosphorus (as a phosphine, phosphite, phosphonate, phosphinate or phosphate group) and carbene groups.

In another aspect, the present invention provides transition metal complexes having at least one ligands which is a cyclic alkyl amino carbene ligand as provided above.

In still other aspects, the present invention provides methods for forming carbon—carbon bonds and carbon—nitrogen bonds in various organic synthesis reactions. In some embodiments, selected complexes of the present invention have particular utility in, for example, amine arylation reactions in which the aryl portion can be essentially any optionally substituted monocyclic or polycyclic aromatic or heteroaromatic component. In other embodiments, selected complexes of the present invention have particular utility in, for example, Suzuki coupling reactions (aryl-aryl or aryl-alkyl coupling reactions) in which each of the aryl portions can be essentially any optionally substituted monocyclic or polycyclic aromatic or heteroaromatic component. In still other embodiments, selected complexes of the present invention have utility in catalyzing α-arylation reaction.

DETAILED DESCRIPTION OF THE INVENTION

Abbreviations and Definitions

Figure 1:
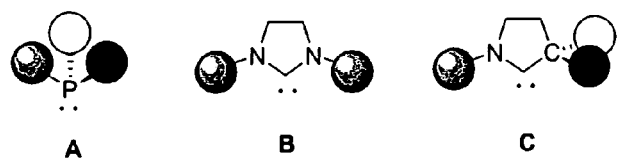
FIG. 1 shows a schematic view of ligands A-C, illustrating their different steric demands.

Abbreviations used herein have their common and accepted meanings to one of skill in the art. Examples of the abbreviations are tBu, tertiary butyl; Me, methyl; THF, tetrahydrofuran; and cod, cyclooctadiene.

In the present description the term "alkyl", alone or in combination, refers to a straight-chain or branched-chain alkyl group having the indicated number of carbon atoms. For example, $C_{1-10}$ alkyl refers to an alkyl group having from one to ten carbon atoms with the remaining valences filled occupied by hydrogen atoms. Preferred alkyl groups are those with 1 to 8 carbon atoms, more preferably a straight or branched-chain alkyl group with 1 to 6 carbon atoms and particularly preferred are straight or branched-chain alkyl groups with 1 to 4 carbon atoms. Examples of straight-chain and branched $C_{1-10}$ alkyl groups are methyl, ethyl, propyl, isopropyl, butyl, isobutyl, tert.-butyl, the isomeric pentyls, the isomeric hexyls, the isomeric heptyls and the like.

The term "cycloalkyl", alone or in combination, refers to a cyclic alkyl group having 3 to 8 carbon atoms as ring vertices. Preferred cycloalkyl groups are those having 3 to 6 carbon atoms. Examples of $C_{3-8}$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl.

The term "alkoxy", alone or in combination, signifies a group of the formula alkyl-O— in which the term "alkyl" has the previously given definition. Examples of alkoxy group include methoxy, ethoxy, n-propoxy, isopropoxy, n-butoxy, isobutoxy, sec-butoxy and tert-butoxy. Preferred alkoxy groups are methoxy and ethoxy.

The term "alkenyl", alone or in combination refers to a straight-chain or branched hydrocarbon residue comprising an olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl.

The term "alkynyl", alone or in combination refers to a straight-chain or branched hydrocarbon residue having a carbon carbon triple bond and the indicated number of carbon atoms. Preferred alkynyl groups have up to 8, preferably up to 6, particularly preferred up to 4 carbon atoms. Examples of alkynyl groups are ethynyl, 1-propynyl, 1-butynyl and 2-butynyl The terms "alkenyloxy" and "alkynyloxy" refer to groups having the formula —O—$R^i$ in which $R^i$ is an alkenyl or alkynyl group, respectively.

The terms "alkylthio," "alkylsulfonyl" and "alkylsulfinyl" refer to groups having the formula —S—$R^i$ —S(O)$_2$—$R^i$ and —S(O)—$R^i$, respectively, in which $R^i$ is an alkyl group as previously defined.

The term "alkoxycarbonyl" refers to a group having the formula —C(O)O—$R^i$, wherein $R^i$ is an alkyl group as defined above and wherein the total number of carbon atoms refers to the combined alkyl and carbonyl moieties.

The term "aryl", alone or in combination, refers to a phenyl or naphthyl group, preferably a phenyl group which optionally carries one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro and the like, such as phenyl, chlorophenyl, trifluoromethylphenyl, chlorofluorophenyl, aminophenyl, methylcarbonylphenyl, methoxyphenyl, methylendioxyphenyl, 1-naphthyl and 2-naphthyl.

The term "aryloxy", alone or in combination, signifies a group of the formula aryl-O— in which the term "aryl" has the previously given significance, such as phenyloxy.

The term "arylalkyl", alone or in combination, refers to an alkyl group as previously defined in which one hydrogen atom has been replaced by an aryl group as previously defined. Preferred are benzyl and phenylethyl.

The term "heteroaryl", alone or in combination, signifies aromatic 5- to 10-membered heterocycle which contains one or more, preferably one or two hetero atoms selected from nitrogen, oxygen and sulfur, wherein nitrogen or oxygen are preferred. If desired, it can be substituted on one or more carbon atoms by halogen, alkyl, alkoxy, cyano, haloalkyl, heterocyclyl, preferably trifluoromethyl. Preferred heteroaryl cycles are pyridinyl or thiophenyl optionaly substituted by one or more, preferably one or two substituents independently selected from halogen, alkyl, alkoxy, cyano, haloalkyl, preferably trifluoromethyl, and heterocyclyl, preferably morpholinyl or pyrrolidinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably amino, dimethylamino and diethylamino and particularly primary amino.

The term "halogen" refers to fluorine, chlorine, bromine or iodine and preferably fluorine, chlorine or bromine.

General

The present invention provides stable cyclic (alkyl)(amino)carbenes (CAACs) C (see FIG. 1). The replacement of one of the electronegative amino substituents of NHCs B by a strong σ-donor alkyl group makes the CAAC ligands even more electron-rich than either the phosphine A or diaminocarbene B ligand families. Moreover, due to the presence of a quaternary carbon in a position α to the carbene center, carbenes C feature steric environments that differentiate them dramatically from both ligands A and B, and amplifies the effect of ligands with flexible steric bulk. As described below, the peculiar electronic and steric properties of carbenes C allow for the synthesis of low coordinate metal species, which are not obtainable with other ligands. Additionally, complexes such as CAAC-palladium complexes exhibit high efficiency for certain reactions including, for example, the catalytic α-arylation of carbonyl compounds.

Cyclic Alkyl Amino Carbenes

In one aspect, the present invention provides cyclic carbenes that are typically stable and which can be isolated. The carbenes are useful as ligands for a variety of transition metal complexes/catalysts. More particularly, the cyclic carbenes are cyclic alkyl amino carbenes (CAAC) and have a carbene center which is flanked by a tertiary amine and a quaternary carbon.

The cyclic alkyl amino carbenes have the formula:

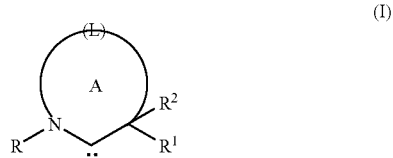

(I)

wherein the A ring is a 4-, 5-, 6- or 7-membered ring; and L is a linking group representing from one to four ring vertices selected from the group consisting of C, O, N, B, Al, P, S and Si with available valences optionally occupied by hydrogen, oxo or $R^a$ substituents.

The letter R represents a member selected from $C_{1-10}$ alkyl, $C_{2-10}$ alkenyl, $C_{2-10}$ alkynyl and aryl, wherein each is optionally substituted with $R^a$ substituents, preferably one to eight $R^a$ substituents and more preferably from one to four $R^a$ substituents.

The symbols $R^1$ and $R^2$ are each members independently selected from $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl and $C_{1-10}$ alkylsulfinyl, or optionally are combined to form a 3- to 12-membered spirocyclic ring, more preferably a 3- to 7-membered spirocyclic ring, wherein the spirocyclic ring is optionally substituted with $R^b$ substituents, preferably with from one to twelve $R^b$ substituents more preferably with from one to eight $R^b$ substituents.

The optional substituents $R^a$ and $R^b$, in each instance, are independently selected from $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl and $C_{1-10}$ alkylsulfinyl. Still other suitable substituents for $R^a$ and $R^b$ are oxo, amino (including mono- and di-alkylamino and acylamino), imines, nitrogen heterocycles (e.g., pyridines), hydroxy, thiol, thiono, phosphorus (as a phosphine, phosphite, phosphonate, phosphinate or phosphate group) and carbene groups.

Turning first to the A ring, preferred rings are those having four, five or six ring members, with five- and six-membered rings being particularly preferred. In the most preferred embodiments, the A ring is a five- or six-membered ring in which L represents two or three carbon vertices, each optionally bearing further substituents as provided above.

Turning next to R, preferred R groups are selected from $C_{1-8}$ alkyl, $C_{2-8}$ alkenyl, $C_{2-8}$ alkynyl and aryl, wherein each is optionally substituted with from one to four $R^a$ substituents. More preferably, R is selected from $C_{1-6}$ alkyl, $C_{2-6}$ alkenyl, $C_{2-6}$ alkynyl and aryl, wherein each is optionally substituted with from one to three $R^a$ substituents. In selected embodiments, each R is $C_{1-6}$ alkyl or aryl, wherein each is optionally substituted with from one to three $R^a$ substituents. In some particularly preferred embodiments, R is phenyl and is optionally substituted with one, two or three $R^a$ substituents. Some preferred substituents are electron-donating substituents such as, for example, $C_{1-6}$ alkyl, $C_{2-6}$ alkenyl, $C_{2-6}$ alkynyl, $C_{1-6}$ alkoxy, $C_{2-6}$ alkenyloxy and $C_{2-6}$ alkynyloxy.

Similarly, the symbols $R^1$ and $R^2$ are each preferably and independently selected from $C_{1-10}$ alkyl, $C_{2-10}$ alkenyl, $C_{2-10}$ alkynyl, aryl and $C_{2-10}$ alkoxycarbonyl, or optionally are combined to form a 3- to 7-membered spirocyclic ring, wherein the spirocyclic ring is optionally substituted with from one to eight $R^b$ substituents. More preferably, $R^1$ and $R^2$ are each independently selected from $C_{1-8}$ alkyl, $C_{2-8}$ alkenyl, $C_{2-8}$ alkynyl and aryl, or optionally are combined to form a 4- to 7-membered spirocyclic ring, still more preferably a 4-, 5-, 6- or 7-membered spirocyclic ring selected from spirocylcobutane, spirocylcopentane, spirocyclohexane and spirocycloheptane, wherein the spirocyclic ring is optionally substituted with from one to four $R^b$ substituents. In selected embodiments, $R^1$ and $R^2$ are each independently selected from $C_{1-8}$ alkyl and aryl, or optionally are combined to form a spirocylcopentane or spirocyclohexane ring, wherein the spirocyclic ring is optionally substituted with from one to four $R^b$ substituents. Preferred $R^b$ substituents are $C_{1-6}$ alkyl, $C_{2-6}$ alkenyl, $C_{2-6}$ alkynyl, phenyl, $C_{1-6}$ alkoxy, $C_{2-6}$ alkenyloxy, $C_{2-6}$ alkynyloxy, phenoxy, $C_{2-6}$ alkoxycarbonyl, $C_{1-6}$ alkylthio, $C_{1-6}$ alkylsulfonyl and $C_{1-6}$ alkylsulfinyl. Further preferred $R^b$ substituents are $C_{1-6}$ alkyl, $C_{2-6}$ alkenyl, $C_{2-6}$ alkynyl, $C_{1-6}$ alkoxy, $C_{2-6}$ alkenyloxy and $C_{2-6}$ alkynyloxy.

One of skill in the art will appreciate that additional embodiments of the invention are those in which combinations of each of the preferred and/or selected groups above are combined.

In certain embodiments, the carbenes have a formula selected from:

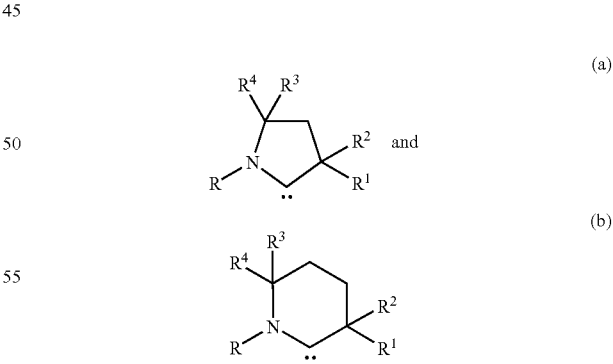

wherein $R^3$ and $R^4$ are each members independently selected from $C_{1-10}$ alkyl, $C_{2-10}$ alkenyl, $C_{2-10}$ alkynyl and aryl, each of which is optionally substituted with from one to four $R^a$ substituents. The remaining R, $R^1$ and $R^2$ groups have the meanings provided above with respect to formula I.

In some embodiments, carbenes are provided having formula (a), while in other embodiments, carbenes are provided having formula (b). With respect to each of formula (a) and (b), preferred carbenes are those in which R is a substituted or unsubstituted aryl group, preferably a substituted or unsubstituted phenyl group, and each of $R^1$, $R^2$, $R^3$ and $R^4$ is independently a $C_{1-6}$ alkyl group.

In other preferred embodiments, carbenes are provided having formula (a) or (b), wherein R is a substituted or unsubstituted aryl group, preferably a substituted or unsubstituted phenyl group; $R^1$ and $R^2$ are combined to form a spirocyclobutane, spirocyclopentane or spirocyclohexane ring, each of which is optionally substituted with from one to four independently selected $C_{1-6}$ alkyl groups; and each of $R^3$ and $R^4$ is independently a $C_{1-6}$ alkyl group.

Preferred substituents for each of the embodiments described above are essentially those that have been provided with reference to formula I above.

In a related aspect, the present invention provides cyclic iminium salts having the formula:

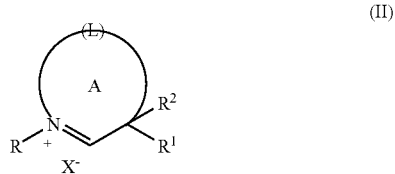

(II)

wherein L, R, $R^1$, $R^2$ and the A ring have the meanings provided above with reference to formula I. Additionally, $X^-$ represents a suitable anion such as, for example, a halide, acetate, trifluoroacetate, mesylate, and the like.

In preferred embodiments, the cyclic iminium salts have the formula:

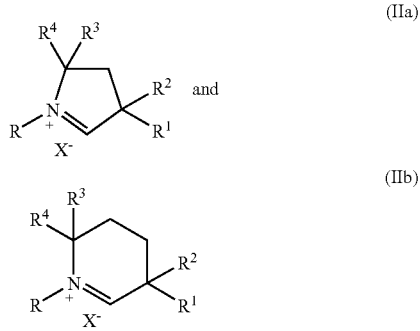

(IIa) and (IIb)

wherein each of R, $R^1$, $R^2$, $R^3$ and $R^4$ have the meanings provided above with respect to formula I, (a) and (b), and $X^-$ is an anion as described above.

One of skill in the art will appreciate that such iminium salts are useful for forming the complexes described herein (whether formed through a carbenoid species or via another route such as oxidative addition).

Transition Metal Complexes

In another aspect, the present invention provides transition metal complexes useful as catalysts in a variety of synthetic organic reactions. In particular, the catalysts or complexes comprise a transition metal and a carbene ligand selected from the carbenes provided above. One of skill in the art will appreciate that such complexes can employ a number of transition metals and have a variety of geometries (e.g., trigonal, square planar, trigonal bipyramidal and the like) depending on the nature of the transition metal and its oxidation state and other factors including, for example, additional ligands.

In general, any transition metal (e.g., a metal having d electrons) can be used to form the complexes/catalysts of the present invention. For example, suitable transition metals are those selected from one of Groups 3-12 of the periodic table or from the lanthanide series. Preferably, the metal will be selected from Groups 5-12 and even more preferably Groups 7-11. For example, suitable metals include platinum, palladium, iron, nickel, iridium, ruthenium and rhodium. The particular form of the metal to be used in the reaction is selected to provide, under the reaction conditions, metal centers which are coordinately unsaturated and not in their highest oxidation state.

To further illustrate, suitable transition metal complexes and catalysts include soluble or insoluble complexes of platinum, palladium, iridium, iron, rhodium, ruthenium and nickel. Palladium, rhodium, iridium, ruthenium and nickel are particularly preferred and palladium is most preferred.

As noted above, the complexes further comprise a carbene ligand as described above with respect to formula (I) and formulae (a) and (b). Preferred carbene ligands are essentially those that have been described as preferred and/or selected embodiments above. The catalyst complex can include additional ligands as required to obtain a stable complex. The additional ligands can be neutral ligands, anionic ligands and/or electron-donating ligands. The ligand can be added to the reaction mixture in the form of a metal complex, or added as a separate reagent relative to the addition of the metal.

Anionic ligands suitable as additional ligands are preferably halide, pseudohalide, tetraphenylborate, perhalogenated tetraphenylborate, tetrahaloborate, hexahalophosphate, hexahaloantimonate, trihalomethanesulfonate, alkoxide, carboxylate, tetrahaloaluminate, tetracarbonylcobaltate, hexahaloferrate(III), tetrahaloferrate(III) or/and tetrahalopalladate(II). Preferably, an anionic ligand is selected from halide, pseudohalide, tetraphenylborate, perfluorinated tetraphenylborate, tetrafluoroborate, hexafluorophosphate, hexafluoroantimonate, trifluoromethanesulfonate, alkoxide, carboxylate, tetrachloroaluminate, tetracarbonylcobaltate, hexafluoroferrate(III), tetrachloroferrate(III) or/and tetrachloropalladate(II). Preferred pseudohalides are cyanide, thiocyanate, cyanate, isocyanate and isothiocyanate. Neutral or electron-donor ligands suitable as additional ligands can be, for example, amines, imines, phosphines, phosphites, carbonyl compounds, alkenyl compounds (e.g., allyl compounds), carboxyl compounds, nitriles, alcohols, ethers, thiols or thioethers. Still other suitable ligands can be carbene ligands such as the diaminocarbene ligands (e.g., NHCs).

While the present invention describes a variety of transition metal complexes useful in catalyzing organic reactions, one of skill in the art will appreciate that many of the complexes can be formed in situ. Accordingly, ligands (either carbene ligands or additional ligands) can be added to a reaction solution as a separate compound, or can be complexed to the metal center to form a metal-ligand complex prior to its introduction into the reaction solution. The additional ligands are typically compounds added to the reaction solution which can bind to the catalytic metal center. In some preferred embodiments, the additional ligand is a chelating ligand. While the additional ligands can provide stability to the catalytic transition metal complex, they may also suppress unwanted side reactions as well as enhance the rate and efficiency of the desired processes. Still further, in some embodiments, the additional ligands can prevent precipitation of the catalytic transition metal. Although the present invention does not require the formation of a metal-additional ligand complex, such complexes have been shown to be consistent with the postulate that they are intermediates in these reactions and it has been observed the selection of the additional ligand has an affect on the course of the reaction.

In related embodiments, the present invention provides metal complexes, of the type described above, in which the carbene ligand has a pendent functionalized side chain (e.g., aminoalkyl, mercaptoalkyl, acyloxyalkyl and the like) in which the functional group acts as a ligand to provide a bidentate ligand feature. In still other embodiments, the carbene ligand forms a metal complex with bidentate ligands that are not tethered to the cyclic carbene moiety.

Reactions Catalyzed by Transition Metal—CAAC Complexes

As noted above, the complexes of the present invention are useful in catalyzing a variety of synthetic organic reactions including amine arylation reactions, Suzuki coupling reactions (aryl-aryl or aryl-alkyl coupling reactions), and α-arylation reactions. Still other reactions that can benefit from the above-noted complexes include, for example, hydroformylation (of alkenes and alkynes), hydrosilylation (of alkenes, alkynes, ketones and aldehydes), metathesis (olefin(RC, CM, ROM, ROMp) ene-yne), carbonylation, hydroarylation and hydroamination.

The reactions of the present invention can be performed under a wide range of conditions, and the solvents and temperature ranges recited herein should not be considered limiting. In general, it is desirable for the reactions to be run using mild conditions which will not adversely affect the reactants, the catalyst, or the product. For example, the reaction temperature influences the speed of the reaction, as well as the stability of the reactants and catalyst. The reactions will typically be run at temperatures in the range of 25° C. to 300° C., more preferably in the range 25° C. to 150° C.

Additionally, the reactions are generally carried out in a liquid reaction medium, but in some instances can be run without addition of solvent. For those reactions conducted in solvent, an inert solvent is preferred, particularly one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

In some embodiments, reactions utilizing the catalytic complexes of the present invention can be run in a biphasic mixture of solvents, in an emulsion or suspension, or in a lipid vesicle or bilayer. In certain embodiments, the catalyzed reactions can be run in the solid phase with one of the reactants tethered or anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivatization with one or more of substituents of the aryl group.

Preparation of Cyclic (Alkyl)(Amino)Carbenes

A versatile, retrosynthetic approach to the CAACs is provided in Scheme 1. The choice of R, $R^1$ and $R^2$ substituents, as well as the ring skeleton provide substantial flexibility in preparing precursors used in the present invention, although $R^1$ and $R^2$ are other than H.

Scheme 1

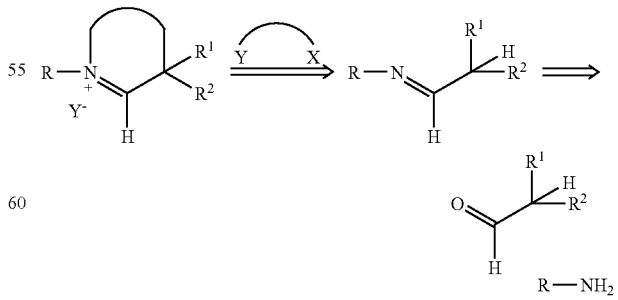

This synthetic strategy was first evaluated as shown in Scheme 2.

Scheme 2

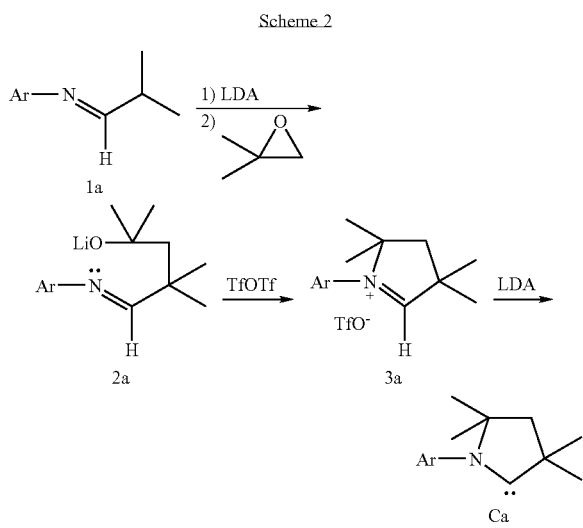

Imine 1a can be prepared from 2,6-di-iso-propylaniline and the simplest aldehyde featuring a secondary alkyl substituent, 2-methylpropanal. Deprotonation with lithium di-iso-propylamide (LDA) afforded the aza-allyl anion, which readily induces the ring opening of 1,2-epoxy-2-methylpropane leading to the corresponding alkoxide 2a. Subsequent treatment with triflic anhydride at −78° C. gives rise to the triflate derivative, which upon warming to room temperature affords the aldiminium salt 3a in 58% yield (based on the imine). Lastly, deprotonation with LDA quantitatively affords carbene Ca as a pale yellow solid. CAAC Ca is stable at room temperature in the solid state and in solution, for at least two weeks.

The presence of the tertiary carbon next to the carbene center offers the ability to construct ligands featuring different types of steric environment. Spiro-CAAC Cb, readily prepared in a manner similar to that used for Ca, but using cyclohexyl carbaldehyde, illustrates how the concept of flexible steric bulk can be incorporated into this ligand family. In fact, compared to the NHCs B developed by Glorius (G. Altenhoff, R. Goddard, C. W. Lehmann, F. Glorius, *J. Am. Chem. Soc.* 126, 15195 (2004)), the cyclohexane ring of Cb is closer to the carbene and to the ensuing metal center, and therefore the effects of the "flexible wing" can be amplified (Scheme 3).

Scheme 3

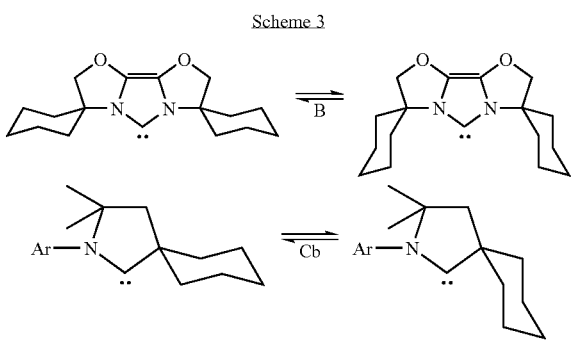

Figure 2:
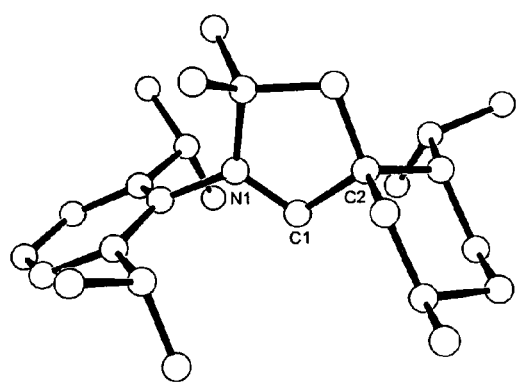
FIG. 2 shows a molecular view of Cc in the solid state. Selected bond lengths and angles are as follows: N1-C1, 1.315±3 Å; C1-C2, 1.516±3 Å; N1-C1-C2, 106.54±18°.

In contrast, carbene Cc exemplifies the rigidity and extreme steric bulk that CAACs can provide to metal centers to which they are bound. As a starting material, the imine derived from (−)-menthone can be used. The key step of the synthesis is based on the well-known propensity of relatively bulky reactants to approach the cyclohexane moiety from the equatorial direction. This effect is reinforced by the presence of the iso-propyl group, and therefore the reaction with the oxirane is completely diastereoselective (Scheme 4). It leads to the diastereomer affording the best protection for the carbene and the ensuing metal center to which it is bound. Moreover, in contrast with Cb, the chair conformation is locked, as the other chair conformation would put both the iso-propyl and methyl groups in unfavorable axial positions (even a boat conformation would be highly adverse). It is apparent from the molecular structure, obtained by a single crystal X-ray diffraction study, that the steric environment of this CAAC is very different from that of phosphines (described as a cone) and NHCs (defined as fan-like) (J. Huang, H. J. Schanz, E. D. Stevens, S. P. Nolan, *Organometallics* 18, 2370 (1999)): the locked cyclohexane moiety constitutes a "wall of protection" not only for the carbene center, but also for a metal when Cc is used as a ligand (FIG. 2). It is noteworthy that Cc is enantiomerically pure and has been prepared without time-consuming enantio- or diastereo-selective separation.

Scheme 4

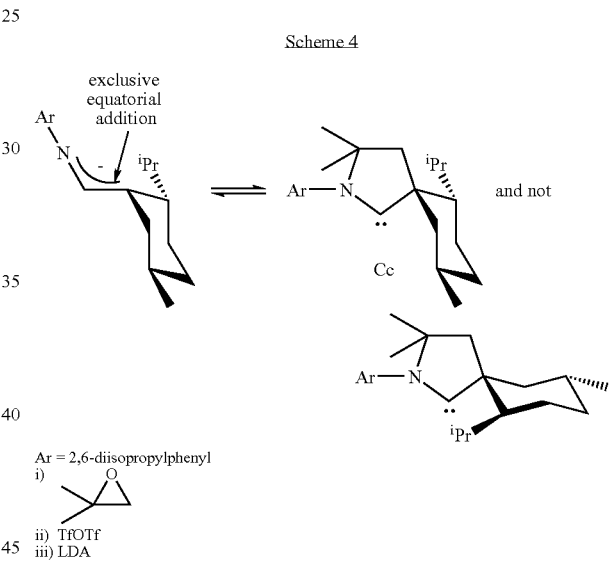

Ar = 2,6-diisopropylphenyl
i) ![epoxide]
ii) TfOTf
iii) LDA

The carbonyl stretching frequencies of cis-[IrCl(CO)$_2$(L)] complexes are recognized as an excellent measure of the σ-donor and π-acceptor properties of the ligand L (A. R. Chianese, A. Kovacevic, B. M. Zeglis, J. W. Faller, R. H. Crabtree, *Organometallics* 23, 2461 (2004)). Addition of half an equivalent of [IrCl(cod)]$_2$ to a THF solution of carbene Cc led to the formation of [IrCl(cod)(Cc)], which upon treatment with CO at room temperature afforded cis-[IrCl(CO)$_2$(Cc)] (4c) in high yield. The average value of the carbonyl stretching frequencies for complex 4c [vv$_{av}$(CO): 2013 cm$^{-1}$] indicates that the donor power of Cc is higher than that of electron-rich phosphines (PCy$_3$: 2028 cm$^{-1}$) and even NHC ligands (2017-2020 cm$^{-1}$); only the abnormal C5-bound NHCs are stronger donors (2003 cm$^{-1}$) (A. R. Chianese, A. Kovacevic, B. M. Zeglis, J. W. Faller, R. H. Crabtree, *Organometallics* 23, 2461 (2004)).

Figure 3:
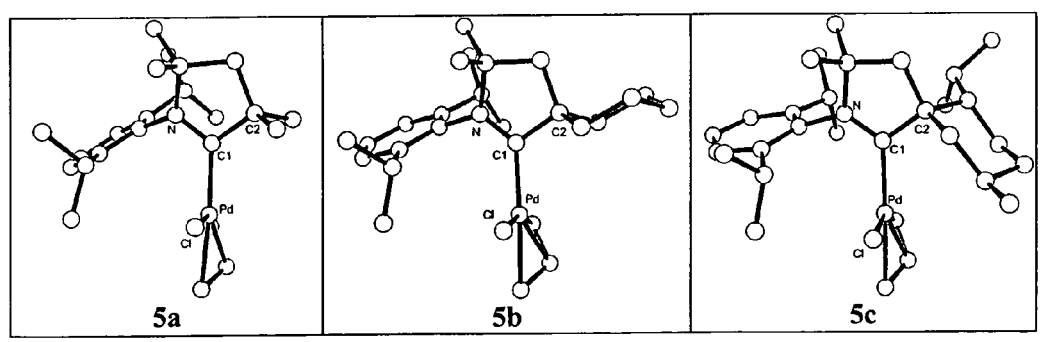
FIG. 3 shows a molecular view of 5a-c in the solid state. Selected bond lengths and angles are as follows: 5a: N—C1, 1.3133±11 Å; C1-C2, 1.5298±12 Å; C1-Pd, 2.0246±9 Å; N—C1-C2, 108.51±8°. 5b: N—C1, 1.310±4 Å; C1-C2, 1.526±4 Å; C1-Pd, 2.020±3 Å; N—C1-C2, 108.7±2°. 5c: N—C1, 1.315±5 Å; C1-C2, 1.543±5 Å; C1-Pd, 2.045±4 Å; N—C1-C2, 108.8±3°.

The steric and electronic properties of CAACs also benefit the numerous catalytic processes, which require bulky electron-rich ligands at the metal center. As an example of such a process, the palladium-catalyzed α-arylation of ketones, discovered concurrently in 1997 by Buchwald (Palucki, S. L. Buchwald, *J. Am. Chem. Soc.* 119, 11108 (1997)); Hartwig (B. C. Hamann, J. F. Hartwig, *J. Am. Chem. Soc.* 119, 12382 (1997)); and Miura (T. Satoh, Y. Kawamura, M. Miura, M. Nomura, *Angew. Chem. Int. Ed.* 36, 1740 (1997)) was evaluated. This reaction has not yet been achieved at room temperature with non-activated aryl chlorides; moreover there are no examples with sterically hindered di-ortho-substituted aryl chlorides. The use of CAAC ligands C, indeed, overcomes these limitations. The [PdCl(allyl)(CAAC)] complexes 5a-c (FIG. 3) were readily prepared in high yields by addition of [Pd(allyl)(Cl)]$_2$ to the corresponding carbenes Ca-c, and isolated as air stable colorless crystals; they can even be purified by column chromatography on silica gel.

Table 1 (see Examples below) summarizes the results obtained using complexes 5a-c for the α-arylation of propiophenone, the classical substrate for such a reaction (see, M. Palucki, S. L. Buchwald, *J. Am. Chem. Soc.* 119, 11108 (1997); B. C. Hamann, J. F. Hartwig, *J. Am. Chem. Soc.* 119, 12382 (1997); M. S. Viciu, R. F. Germaneau, S. P. Nolan, *Org. Lett.* 4, 4053 (2002); J. M. Fox, X. H. Huang, A. Chieffi, S. L. Buchwald, *J. Am. Chem. Soc.* 122, 1360 (2000); and A. Ehrentraut, A. Zapf, M. Beller, *Adv. Synth. Catal.* 344, 209 (2002)). With non-hindered aryl chlorides, entries 1-8 demonstrate the superior catalytic activity of CAAC complex 5c over 5a,b. A turn over number (TON) of up to 7200 has been obtained at room temperature. This compares extremely favorably with the best TON reported so far: 4200 at 120° C. (A. Ehrentraut, A. Zapf, M. Beller, *Adv. Synth. Catal.* 344, 209 (2002)). When a di-ortho-substituted aryl chloride is used (entries 9-14), catalytic activity of 5b is greater than that of 5a and 5c, even at room temperature. Entries 11 and 13 show the thermal stability of the catalyst.

Without intending to be bound by theory, the dramatic differences observed in the catalytic activity of complexes 5a-c can be rationalized by the different steric environments created by ligands Ca, Cb and Cc. Carbene Ca is not sterically hindered enough to favor reductive elimination at room temperature. This step is easily promoted, for relatively small coupling substrates, by the very rigid and bulky Cc ligand. However, entry 14 shows that Cc gives rise to a catalyst very sensitive to excessive steric hindrance. The molecular structures shown in FIG. 3 clearly show that the steric environment around the metal is very similar for 5a and 5b, and therefore cannot explain the superior catalytic activity of 5b. However, in solution, the cyclohexane moiety of 5b can easily undergo a ring flip, which leads to a steric environment very similar to that of 5c. This flexibility also explains the superiority of 5b over 5c to accommodate sterically demanding substrates in the coupling process.

Although the α-arylation of carbonyl compounds has a broad scope of application (D. A. Culkin, J. F. Hartwig, *Acc. Chem. Res.* 36, 234 (2003)), very little success has been reported with aldehydes (Y. Terao, Y. Fukuoka, T. Satoh, M. Miura, M. Nomura, *Tetrahedron Lett.* 43, 101 (2002)), mostly because of the competing aldol condensation. Using the mild conditions allowed by the CAAC palladium complexes, this side reaction could be reduced. Indeed, 2-chlorotoluene is coupled with isobutanal with high efficiency at ambient temperature. Using 1 mol/% of 5c, the adduct was obtained after 16 h in 98% yield, and no evidence for aldol condensation products was observed. This is the first example of α-arylation of an aldehyde with an aryl chloride.

Figure 4:
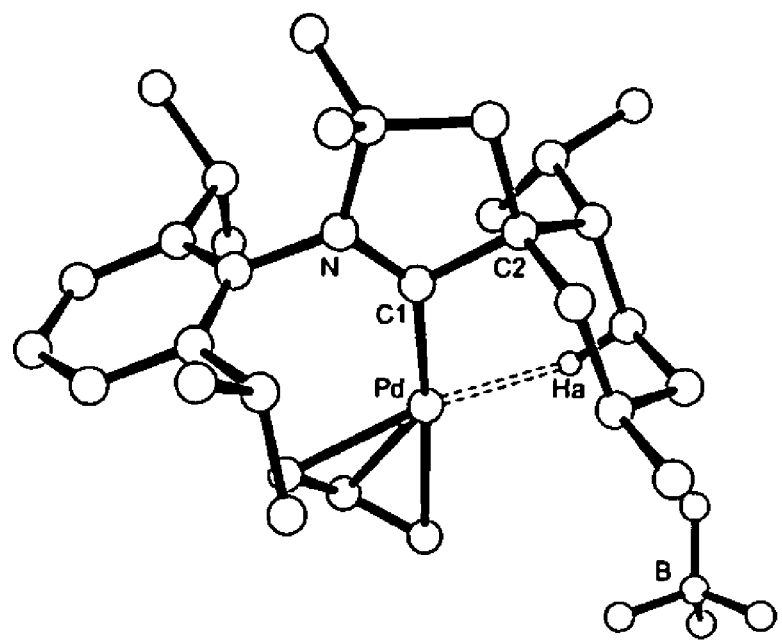
FIG. 4 shows a molecular view of 6 in the solid state. Selected bond lengths and angles are as follows: N—C1, 1.293±3 Å; C1-C2, 1.519±3 Å; C1-Pd, 2.038±3 Å; Pd-Ha, 2.052; N—C1-C2, 109.4±2°.

The high turn over numbers obtained with 5c might suggest that ligand Cc is able to stabilize low coordinate metal species, which play a key role in catalytic processes. Although, the mono-ligated 12-electron palladium(0) complex [the postulated active catalyst (W. A. Herrmann, in *Applied Homogeneous Catalysis with Organometallic Compounds. A Comprehensive Handbook*, B. Cornils, W. A. Herrmann, Eds. (VCH, Weinheim) vol. 1, 722 (1996); and V. V. Grushin, H. Alper in *Activation of Unreactive Bonds and Organic Synthesis*, S. Murai, Ed. (Springer, Berlin) 203 (1999))] has not been characterized, a cationic 14-electron palladium(II) complex 6 has been prepared by treatment of 5c with a stoichiometric amount of AgBF$_4$. Previous attempts to isolate such cationic species using other ligands failed (Y. Ding, R. Goddard, K. R. Pörschke, *Organometallics* 24, 439 (2005); and M. S. Viciu, F. K. Zinn, E. D. Stevens, S. P. Nolan, *Organometallics* 22, 3175 (2003)). The single crystal X-ray diffraction study of 6 shows no interaction with the anion but an agostic interaction with the axial Ha atom (Pd-Ha: 2.05 Å) (FIG. 4). Therefore, the rigid cyclohexane moiety not only provides a wall of protection (steric effects), but also an electronic stabilization to the palladium center, when it is low-ligated as in its catalytic form.

Figure 5:
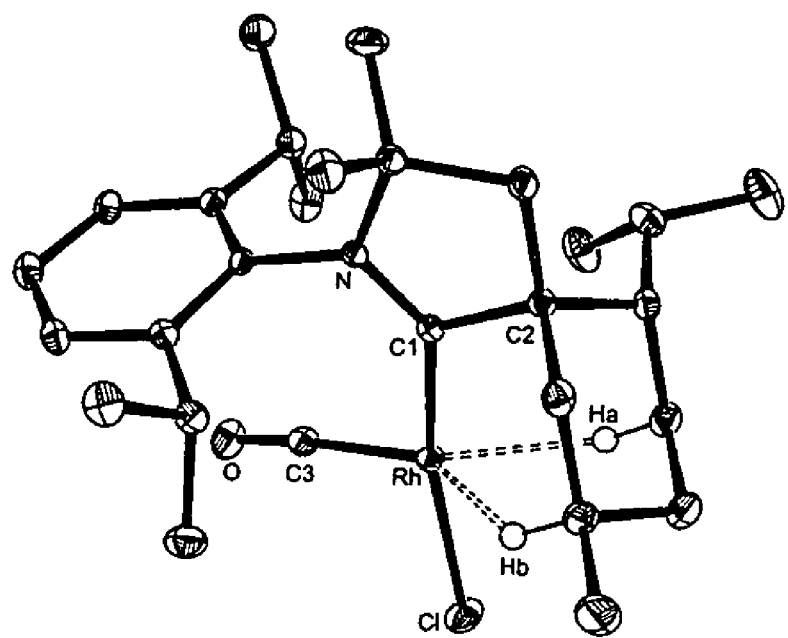
FIG. 5 shows a molecular view of 7 in the solid state. Selected bond lengths and angles are as follows: N—C1, 1.3174±14 Å; C1-C2, 1.5368±15 Å; C1-Rh, 1.9399±10 Å; Rh-C1, 2.3740±3 Å; Rh-C3, 1.7955±11 Å; C3-O, 1.1433±14 Å; Rh-Ha, 2.183±17 Å; Rh-Hb, 2.231±17 Å; N—C1-C2, 108.70±9°.

The unique properties of CAACs are, of course, not only apparent with group 10 metals. For example, the addition of the rigid CAAC Cc to [RhCl(cod)$_2$]$_2$, followed by treatment with excess CO, or even direct addition of Cc to [RhCl(CO)$_2$]$_2$, do not lead to the classical di-carbonyl 16-electron RhCl(CO)$_2$(Cc) complex (M. Mayr, K. Wurst, K.-H. Ongania, M. Buchmeiser, *Chem. Eur. J.* 10, 1256 (2004)), but to the monomeric mono-carbonyl 14-electron complex RhCl(CO)(Cc) 7, which is amazingly air and thermally stable. As for palladium complex 6, complex 7 is stabilized by agostic interactions with axial H atoms of the cyclohexane ring (Rh1-Ha: 2.18, Rh-Hb: 2.23 Å) (FIG. 5). Related RhClL$_2$ complexes, exemplified by the active species of Wilkinson's catalyst [RhCl(PPh$_3$)$_2$], are known as transient species (J. P. Collman, L. S. Hegedus, J. R. Norton, R. G. Finke, Eds., *Principles and Applications of Organotransition Metal Chemistry* (University Science Books, Mill Valley, Calif., 1987)). They can only be generated in situ by ligand dissociation or by hapticity changes; otherwise they readily form chloro-bridged dimers (G. Canepa, C. D. Brandt, H. Werner, *J. Am. Chem. Soc.* 124, 9666 (2002)), even when two very bulky ligands L are present (K. Wang, G. P. Rosini, S. P. Nolan, A. S. Goldman, *J. Am. Chem. Soc.* 117, 5082 (1995)).

In recent years, several different types of stable carbenes have been prepared (Y. Canac, M. Soleilhavoup, S. Conejero, G. Bertrand, *J. Organomet. Chem.* 689, 3857 (2004); and W. Kirmse, *Angew. Chem. Int. Ed.* 43, 1767 (2004)), but only NHCs, when used as ligands, have led to highly active and robust catalysts, which compete or even surpass their bulky, electron-rich phosphine counterparts. The readily available CAACs have now entered the realm of alternatives to both of these ligands. Their unique steric and electronic properties, in addition to the broad range of structural features possible, which arise as a result of the presence of a tertiary carbon in a position α to the carbene center, makes these carbenes highly desirable as ligands for various catalytic processes, including asymmetric variants.

EXAMPLES

Synthesis and Spectroscopic Data

All manipulations were performed under an inert atmosphere of argon using standard Schlenk techniques. Dry,

Example 1

This example provides the preparation of selected Imines 1.

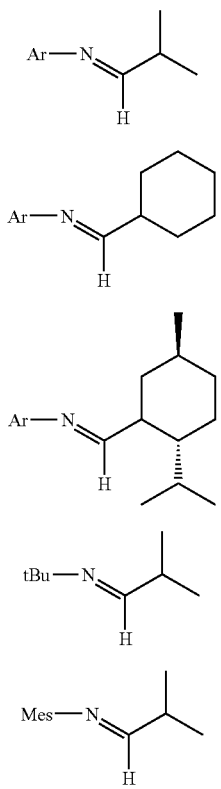

Imine 1a has already been described (Brookhart, M.; Daugulis, O. PCT Int. Appl. (2003), CODEN: PIXXD2 WO 2003078478 A1 20030925).

Imine 1b: In a schlenk tube containing activated molecular sieves (3 g), the aldehyde (7.13 mL, 59.2 mmol) was added dropwise to a solution of 2,6-diisopropylaniline (10.0 g, 56.4 mmol) in toluene (60 mL). The suspension was stirred for 12 hours at room temperature. After filtration, the molecular sieves was washed with hexane (30 mL). Evaporation of the solvent under vacuum, afforded 1b as a white solid, which was recrystallized in pentane at 0° C. (13.75 g, 90%, m.p. 93-95° C.). $^1$H NMR (CDCl$_3$, 25° C.): 7.51 (d, 1H, CH, J=4.8), 7.04-7.14 (m, 3H, H$_{ar}$), 2.95 (sept, 2H, CHCH$_3$, J=6.9), 2.47 (m, 1H, CH), 2.00 (m, 2H, CH$_2$), 1.87 (m, 2H, CH$_2$), 1.75 (m, 1H, CH$_2$), 1.20-1.50 (m, 5H, CH$_2$), 1.17 (d, 12H, CHCH$_3$, J=6.9). $^{13}$C NMR (CDCl$_3$, 25° C.): 171.26 (CH), 149.28 (C$_{ar}$), 137.73 (C$_{ar}$), 123.94 (C$_{ar}$), 123.00 (C$_{ar}$), 44.45 (CH), 29.59 (CH$_2$), 27.77 (CH), 26.23 (CH$_2$), 25.67 (CH$_2$), 23.65 (CH$_3$).

Imine 1c: In a schlenk tube containing activated molecular sieves (10 g), the aldehyde (Spino, C.; Beaulieu, C. Angew. Chem. Int. Ed. 2000, 39, 1930) (33.77 mL, 181.2 mmol) was added dropwise to a solution of 2,6-diisopropylaniline (30.6 g, 172.5 mmol) in toluene (100 mL). The suspension was stirred for 12 hours at 100° C. After filtration, the molecular sieves was washed with hexane (60 mL). Evaporation of the solvent and then heating under vacuum at 100° C., to remove all volatiles, afforded 1c as a yellow oily solid (52.01 g, 92%) and as a mixture of two diastereoisomers (90/10). Major diastereoisomer. $^1$H NMR (CDCl$_3$, 25° C.): 7.42 (d, 1H, CH, J=6.9), 7.03-7.13 (m, 3H, H$_{ar}$), 2.96 (sept, 2H, CHCH$_3$, J=6.6), 2.50 (m, 1H, CH), 1.69-1.90 (m, 4H), 1.00-1.56 (m, 5H), 1.17 (d, 6H, CHCH$_3$, J=6.6), 1.15 (d, 6H, CHCH$_3$, J=6.6), 0.97 (d, 3H, CHCH$_3$, J=6.6), 0.94 (d, 3H, CHCH$_3$, J=6.6), 0.88 (d, 3H, CHCH$_3$, J=6.9). $^{13}$C NMR (CDCl$_3$, 25° C.): 171.60 (CH), 148.86 (C$_{ar}$), 138.01 (C$_{ar}$), 124.01 (C$_{ar}$), 123.04 (C$_{ar}$), 48.44 (CH), 45.24 (CH), 39.18 (CH$_2$), 34.96 (CH$_2$), 32.30, 29.48, 27.70, 23.90, 23.70 (CH$_2$), 23.68, 22.77, 21.62, 15.48.

Additional imines (1d and 1e) can be prepared as described in Stevens, C. V.; Peristeropoulou, M.; DeKimpe, N. *Tetrahedron* 2001, 57, 7865 and Daugulis, O.; Brookhart, M. *Organometallics*, 2002, 21, 5926, respectively.

Example 2

This example provides the preparation of Iminium salts 3.

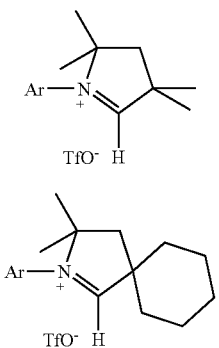

Iminium salt 3a: A solution of LDA (4.66 g, 43.5 mmol) in Et$_2$O (40 mL) was added at 0° C. to a stirred solution of imine 1a (10.05 g, 43.5 mmol) in Et$_2$O (40 mL). The solution was warmed up to room temperature and stirred for 2 hours. After evaporation of the solvent under vacuum, the residue was dissolved in Et$_2$O (80 mL), and 1,2-epoxy-2-methylpropane (4.06 mL, 45.7 mmol) was added dropwise. After stirring for 12 hours at room temperature, trifluoromethane sulfonic anhydride (Tf$_2$O) (7.68 mL, 45.7 mmol) was added at −78° C. The solution was warmed to room temperature and stirred for 1 hour. After filtration, the remaining solid was washed with Et$_2$O (80 mL). Extraction with CH$_2$Cl$_2$ (40 mL) afforded 3a as a white solid (10.99 g, 58%, m.p. 198-200° C.). $^1$H NMR (CDCl$_3$, 25° C.): 9.48 (s, 1H, CH), 7.53 (m, 1H, H$_{ar}$), 7.34 (m, 2H, H$_{ar}$), 2.63 (sept, 2H, CHCH$_3$, J=6.9), 2.43 (s, 2H, CH$_2$), 1.68 (s, 6H, CH$_3$), 1.54 (s, 6H, CH$_3$), 1.35 (d, 6H, CHCH$_3$, J=6.9), 1.17 (d, 6H, CHCH$_3$, J=6.9). $^{13}$C NMR (CD$_3$CN, 25° C.): 192.19 (CH), 145.64 (C$_{ar}$), 133.09 (C$_{ar}$), 130.07 (C$_{ar}$), 126.58 (C$_{ar}$), 122.15 (q, CF$_3$SO$_3^-$, J=321.6), 85.82 (C), 66.34 (C), 48.84 (CH$_2$), 30.39, 28.47, 26.28, 26.18, 22.24.

Iminium salt 3b: A solution of LDA (3.87 g, 36.1 mmol) in Et$_2$O (40 mL) was added at 0° C. to a stirred solution of imine 1b (9.79 g, 36.1 mmol) in Et$_2$O (40 mL). The solution was warmed up to room temperature and stirred for 2 hours. After evaporation of the solvent under vacuum, the residue was dissolved in Et$_2$O (100 mL), and 1,2-epoxy-2-methylpropane (3.37 mL, 37.9 mmol) was added dropwise. After stirring for 12 hours at room temperature, Tf$_2$O (6.38 mL, 37.9 mmol) was added at −78° C. The solution was warmed to room temperature and stirred for 1 hour. After filtration, the remaining solid was washed with Et$_2$O (80 mL) to give 3b as a white solid (8.25 g, 48%, m.p. 268-270° C.). $^1$H NMR (CD$_3$CN, 25° C.): 8.91 (s, 1H, CH), 7.67 (m, 1H, H$_{ar}$), 7.52 (m, 2H, H$_{ar}$), 2.78 (sept, 2H, CHCH$_3$, J=6.9), 2.53 (s, 2H, CH$_2$), 1.19-2.11 (m, 10H, CH$_2$), 1.59 (s, 6H, CH$_3$), 1.40 (d, 6H, CHCH$_3$, J=6.9), 1.15 (d, 6H, CHCH$_3$, J=6.9). $^{13}$C NMR (CD$_3$CN, 25° C.): 191.27 (CH), 145.45 (C$_{ar}$), 132.88 (C$_{ar}$), 130.04 (C$_{ar}$), 126.37 (C$_{ar}$), 122.17 (q, CF$_3$SO$_3^-$, J=321.2), 84.98 (C), 53.63 (C), 45.87 (CH$_2$), 34.56 (CH$_2$), 30.22, 28.74, 26.06, 25.27 (CH$_2$), 22.07.

Iminium salt 3c: A solution of the lithium salt of dimethylamine (1.56 g, 30.5 mmol) in THF (40 mL) was added at 0° C. to a stirred solution of imine 1c (10.00 g, 30.5 mmol) in THF (40 mL). The solution was warmed up to room temperature and stirred for 18 hours. After evaporation of the solvent and then heating under vacuum at about 200° C. for 10 minutes to remove the thf complexed to the lithium, the residue was dissolved in toluene (100 mL). After adding dropwise 1,2-epoxy-2-methylpropane (2.85 mL, 32.0 mmol), the solution was stirred for 12 hours at room temperature. Then Tf$_2$O (5.39 mL, 32.0 mmol) was added at −78° C. and the suspension was allowed to warm up to room temperature and stirred for 2 hours. After filtration, the oily residue was washed with boiling toluene (90 mL). Extraction with CH$_2$Cl$_2$ (60 mL) afforded 3c as a white solid (6.65 g, 41%), which was recrystallized in CH$_2$Cl$_2$/Et$_2$O at −20° C. (m.p. 258-260° C.). [α]$_D^{23}$=−38° (CHCl$_3$). $^1$H NMR (CDCl$_3$, 25° C.): 9.73 (s, 1H, CH), 7.53 (m, 1H, H$_{ar}$), 7.34 (m, 2H, H$_{ar}$), 2.64 (m, 3H, CH), 2.20 (m, 2H), 2.04 (m, 2H), 1.90 (m, 2H), 1.78 (m, 2H), 1.59 (s, 3H, CH$_3$), 1.55 (s, 3H, CH$_3$), 1.35 (d, 3H, CHCH$_3$, J=7.0), 1.34 (d, 3H, CHCH$_3$, J=6.0), 1.21 (d, 3H, CHCH$_3$, J=6.5), 1.17 (d, 3H, CHCH$_3$, J=6.0), 1.06 (d, 3H, CHCH$_3$, J=7.0), 1.00-1.10 (m, 2H), 0.94 (d, 3H, CHCH$_3$, J=6.5), 0.83 (d, 3H, CHCH$_3$, J=6.5). $^{13}$C NMR (CDCl$_3$, 25° C.): 192.64 (CH), 144.71 (C$_{ar}$), 144.54 (C$_{ar}$), 131.74 (C$_{ar}$), 128.97 (C$_{ar}$), 125.59 (C$_{ar}$), 125.06 (C$_{ar}$), 120.57 (q, CF$_3$SO$_3^-$, J=321.6), 81.65 (C), 58.51 (C), 52.16 (CH$_2$), 50.97 (CH), 45.43 (CH$_2$), 34.68 (CH$_2$), 29.91, 29.48, 29.17, 28.13, 27.10, 26.69, 25.52, 22.82, 22.67, 22.30 (CH$_2$), 22.24, 22.11, 18.66.

Iminium salt 3d: A solution of LDA (8.43 g, 78.7 mmol) in Et$_2$O (60 ml) was added at 0° C. to a stirred solution of imine 1d (10.00 g, 78.7 mmol) in Et$_2$O (60 ml). The solution was warmed up to room temperature and stirred for 2 hours. After evaporation of the solvent under vacuum, the residue was dissolved in Et$_2$O (150 ml), and 1,2-epoxy-2-methylpropane (7.34 ml, 82.7 mmol) was added dropwise. After stirring for 12 hours at room temperature, Tf$_2$O (13.91 ml, 82.7 mmol) was added at −78° C. The solution was allowed to warm up to room temperature and stirred for 1 hour. After filtration, the remaining solid was washed with Et$_2$O (100 ml) to give 3d as a white solid (15.39 g, 59%). $^1$H NMR (CD$_3$CN, 25° C.): 8.64 (s, 1H, CH), 2.17 (s, 2H, CH$_2$), 1.74 (s, 6H, CH$_3$), 1.65 (s, 9H, CH$_3$), 1.40 (s, 6H, CH$_3$). $^{13}$C NMR (CD$_3$CN, 25° C.): 185.22 (CH), 120.58 (q, CF$_3$SO$_3^-$, J=319.3), 82.67 (C), 67.61 (C), 51.97 (CH$_2$), 44.72 (C), 29.77 (CH$_3$), 29.41 (CH$_3$), 24.96 (CH$_3$).

Iminium salt 3e: A solution of LDA (4.82 g, 45.0 mmol) in Et$_2$O (50 ml) was added at 0° C. to a stirred solution of imine 1e (8.50 g, 45.0 mmol) in Et$_2$O (50 ml). The solution was warmed up to room temperature and stirred for 2 hours. After evaporation of the solvent under vacuum, the residue was dissolved in Et$_2$O (100 ml), and 1,2-epoxy-2-methylpropane (4.19 ml, 47.2 mmol) was added dropwise. After stirring for 12 hours at room temperature, Tf$_2$O (7.94 ml, 47.2 mmol) was added at −78° C. The solution was allowed to warm up to room temperature and stirred for 1 hour. After filtration, the remaining solid was washed with Et$_2$O (60 ml) to give 3e as a white solid (10.79 g, 61%). $^1$H NMR (CDCl$_3$, 25° C.): 9.15 (s, 1H, CH), 7.00 (s, 2H, H$_{ar}$), 2.38 (s, 2H, CH$_2$), 2.30 (s, 3H, CH$_3$), 2.20 (s, 6H, CH$_3$), 1.63 (s, 6H, CH$_3$), 1.54 (s, 6H, CH$_3$). $^{13}$C NMR (CDCl$_3$, 25° C.): 192.77 (CH), 141.21 (C$_{ar}$), 133.30 (C$_{ar}$), 130.75 (C$_{ar}$), 130.31 (C$_{ar}$), 120.88 (q, CF$_3$SO$_3^-$, J=319.0), 84.39 (C), 49.19 (CH$_2$), 48.11 (C), 28.60 (CH$_3$), 26.54 (CH$_3$), 21.03 (CH$_3$), 19.27 (CH$_3$).

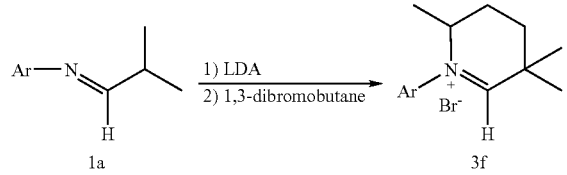

Iminium salt 3f: A solution of LDA (2.80 g, 26.2 mmol) in Et$_2$O (30 ml) was added at 0° C. to a stirred solution of imine 1a (6.05 g, 26.2 mmol) in Et$_2$O (30 ml). The solution was warmed up to room temperature and stirred for 2 hours. After evaporation of the solvent under vacuum, the residue was dissolved in Et$_2$O (50 ml), and 1,3-dibromobutane (3.30 ml, 27.5 mmol) was added dropwise. The solution was allowed to warm up to room temperature and stirred for 12 hours. After filtration and evaporation of the solvent under vacuum, the residue was dissolved in toluene (40 ml). Then heating at 110° C. for 1 hour and filtration afforded 3f as a white solid (7.58 g, 79%). $^1$H NMR (CDCl$_3$, 25° C.): 9.54 (s, 1H, CH), 7.32 (m, 1H, H$_{ar}$), 7.12 (m, 2H, H$_{ar}$), 4.09 (m, 1H, CHCH$_3$), 2.47 (sept, 1H, CHCH$_3$, J=6.9), 2.33 (sept, 1H, CHCH$_3$, J=6.9), 2.23 (m, 1H, CH$_2$), 1.65-2.00 (m, 3H, CH$_2$), 1.45 (s, 3H, CH$_3$), 1.44 (s, 3H, CH$_3$), 1.14-1.19 (m, 9H, CHCH$_3$), 1.11 (d, 3H, CHCH$_3$, J=6.9), 1.03 (d, 3H, CHCH$_3$, J=6.9). $^{13}$C NMR (CDCl$_3$, 25° C.): 190.67 (CH), 142.49 (C$_{ar}$), 141.88 (C$_{ar}$), 136.06 (C$_{ar}$), 131.38 (C$_{ar}$), 125.11 (C$_{ar}$), 124.79 (C$_{ar}$), 62.45 (CH), 38.31 (C), 28.86, 28.81, 28.32 (CH$_2$), 25.79 (CH$_2$), 25.59, 25.42, 25.12, 22.86, 22.38, 17.63.

Example 3

This example illustrates the preparation of representative carbenes.

Carbene Ca: A 1/1 mixture of LDA and iminium salt 3a (5.0 mmol) was cooled to −78° C. and 30 mL of THF was added. The suspension was warmed to room temperature and stirred for 30 min. After evaporation of the solvent under vacuum, a solid residue containing Ca and LiOTf was obtained and used for the complexation reaction without further purification. $^{13}$C NMR (thf-d$_8$, 25° C.): 304.22 (C), 145.81 (C$_{ar}$), 137.51 (C$_{ar}$), 128.05 (C$_{ar}$), 123.77 (C$_{ar}$), 82.47 (C), 57.75 (C), 50.35 (CH$_2$), 29.09, 28.89, 27.49, 21.75.

Carbene Cb: A 1/1 mixture of LDA and iminium salt 3b (5.0 mmol) was cooled to −78° C. and 30 mL of THF was added. The suspension was warmed to room temperature and stirred for 30 min. After evaporation of the solvent under vacuum, a solid residue containing Cb and LiOTf was obtained and used for the complexation reaction without further purification. $^{13}$C NMR (thf-d$_8$, 25° C.): 309.43 (C), 145.80 (C$_{ar}$) 137.84 (C$_{ar}$), 127.87 (C$_{ar}$), 123.57 (C$_{ar}$), 81.23 (C), 63.29 (C), 47.70 (CH$_2$), 35.85 (CH$_2$), 29.33, 29.15, 26.42 (CH$_2$), 22.99 (CH$_2$), 21.55.

Carbene Cc: A 1/1 mixture of LDA and iminium salt 3c (1.40 g, 2.6 mmol) was cooled to −78° C. and 20 mL of toluene was added. The suspension was warmed to room temperature and stirred for 30 min. After evaporation of the solvent under vacuum, the solid residue was extracted with hexane (30 mL). Evaporation of the solvent under vacuum, afforded Cc as a white microcrystalline solid (0.92 g, 92%, m.p. 115° C.). [α]$_D^{23}$=+113° (hexane). $^1$H NMR (C$_6$D$_6$, 25° C.): 7.13-7.25 (m, 3H, H$_{ar}$), 3.18 (sept, 2H, CHCH$_3$, J=6.9), 2.54-2.78 (m, 2H), 2.11 (m, 1H), 1.72-1.97 (m, 4H), 1.41 (dd, 1H, J=12.3 and J=3.3), 1.11-1.27 (m, 21H), 1.06 (d, 3H, CHCH$_3$, J=6.9), 1.02 (d, 3H, CHCH$_3$, J=6.9), 0.96 (3H, CHCH$_3$, J=6.6). $^{13}$C NMR (thf-d$_8$, 25° C.): 319.00 (C), 146.60 (C$_{ar}$), 145.70 (C$_{ar}$), 138.10 (C$_{ar}$), 127.64 (C$_{ar}$), 123.78 (C$_{ar}$), 123.31 (C$_{ar}$), 79.67 (C), 69.45 (C), 53.09 (CH$_2$), 52.03 (CH), 47.98 (CH$_2$), 36.90 (CH$_2$), 30.19, 29.76, 29.11, 29.02, 28.61, 27.75, 26.96, 25.44, 24.12 (CH$_2$), 23.62, 22.85, 21.97, 21.23, 18.70.

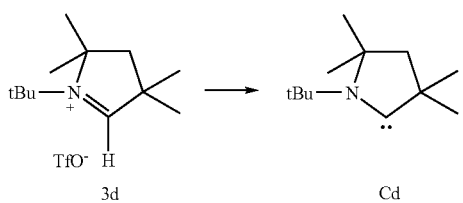

Carbene Cd: A 1/1 mixture of LDA and iminium salt 3d (5.0 mmol) was cooled to −78° C. and 30 ml of THF was added. The suspension was warmed to room temperature and stirred for 30 min. After evaporation of the solvent under vacuum, a solid residue containing Cd and LiOTf was obtained (quantitative by $^{13}$C NMR). $^{13}$C NMR (thf-d$_8$, 25° C.): 301.94 (C), 80.58 (C), 61.35 (C), 55.92 (CH$_2$), 53.25 (C), 32.89 (CH$_3$), 31.45 (CH$_3$), 27.25 (CH$_3$).

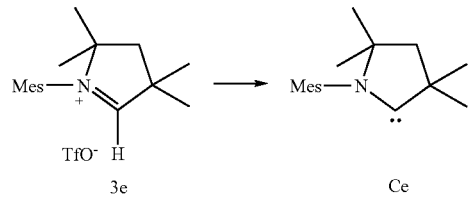

Carbene Ce: A 1/1 mixture of LDA and iminium salt 3e (5.0 mmol) was cooled to −78° C. and 30 ml of THF was added. The suspension was warmed to room temperature and stirred for 30 min. After evaporation of the solvent under vacuum, a solid residue containing Ce and LiOTf was obtained. $^{13}$C NMR (thf-d$_8$, 25° C.): 288.00 (C).

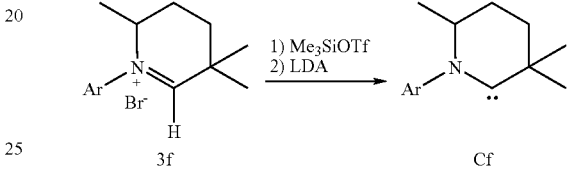

Carbene Cf: Me$_3$SiOTf (0.90 ml, 5.0 mmol) was added at −78° C. to a solution of iminiun bromide 3f (1.83 g, 5.0 mmol) in CH$_2$Cl$_2$ (30 ml). The suspension was warmed to room temperature and stirred for 1 hour. After evaporation of the solvent, a solid residue was obtained. Then to a 1/1 mixture of LDA and iminium triflate (5.0 mmol), 30 ml of THF was added at −78° C. The suspension was warmed to room temperature and stirred for 30 min. After evaporation of the solvent under vacuum, a solid residue containing carbene Cf and LiOTf was obtained. $^1$H NMR (thf-d$_8$, 25° C.): 7.00-7.20 (m, 3H, H$_{ar}$), 3.34 (m, 1H, CHCH$_3$), 2.85 (sept, 2H, CHCH$_3$, J=6.9), 1.85-1.96 (m, 1H, CH$_2$), 1.29-1.62 (m, 3H, CH$_2$), 1.18 (d, 3H, CHCH$_3$, J=6.9), 1.14 (d, 3H, CHCH$_3$, J=6.9), 1.11 (s, 3H, CH$_3$), 1.04 (s, 3H, CH$_3$), 1.00 (d, 3H, CHCH$_3$, J=6.6), 0.98 (d, 3H, CHCH$_3$, J=6.3), 0.94 (d, 3H, CHCH$_3$, J=6.3). $^{13}$C NMR (thf-d$_8$, 25° C.): 322.00 (C), 144.45 (C$_{ar}$), 144.02 (C$_{ar}$), 142.35 (C$_{ar}$), 126.86 (C$_{ar}$), 123.44 (C$_{ar}$), 123.37 (C$_{ar}$), 56.15 (CH), 41.88 (C), 28.39, 28.26, 27.95, 27.12 (CH$_2$), 26.88 (CH$_2$), 26.47, 24.64, 23.91, 22.21, 21.70, 18.34.

Example 4

This example illustrates the preparation of representative transition metal complexes of the invention.

IrCl(CO)$_2$(Cc) Complex (4c)

A solution of carbene Cc (0.34 g, 0.90 mmol) in THF (5 mL) was added at −78° C. to a stirred THF solution (5 mL) of bis[μ-chloro(1,5-cyclooctadiene)iridium(I)] (0.27 g, 0.41 mmol). The solution was warmed to room temperature and stirred for 3 hours. After evaporation of the solvent under vacuum, the residue was washed with hexane (15 mL). Then, it was dissolved in THF (5 mL) and carbon monoxide was bubbled through the solution (45 min) at room temperature. After evaporation of the solvent under vacuum, carbene complex 4c was obtained as a brown powder (0.42 g, 71%). $^1$H NMR (CDCl$_3$, 25° C.): 7.55 (m, 1H, H$_{ar}$), 7.36 (m, 2H, H$_{ar}$), 2.61-2.76 (m, 3H), 2.38 (d, 1H, J=14.4), 2.06-2.24 (m, 3H), 1.67-1.95 (m, 6H), 1.64 (s, 3H), 1.60 (s, 3H), 1.36 (d, 6H, CHCH$_3$, J=6.6), 1.19-1.27 (m, 6H), 1.08 (d, 3H, CHCH$_3$, J=6.9), 0.97 (d, 3H, CHCH$_3$, J=5.4), 0.85 (d, 3H, CHCH$_3$, J=6.9). $^{13}$C NMR (CDCl$_3$, 25° C.): 191.32 (CO), 190.86 (C), 167.80 (CO), 144.83 (C$_{ar}$), 144.67 (C$_{ar}$), 132.28 (C$_{ar}$), 129.03 (C$_{ar}$), 126.12 (C$_{ar}$), 125.58 (C$_{ar}$), 82.36 (C), 58.74, 58.62, 52.32, 51.08, 45.78, 34.59, 30.38, 30.12, 29.71, 28.64, 27.58, 27.39, 26.60, 23.28, 23.02, 22.90, 22.50, 22.20, 19.36. IR (CH$_2$Cl$_2$): υ(CO) 2055, 1971 cm$^{-1}$.

PdCl(Allyl)(C) Complexes (5)

PdCl(Allyl)(Ca) complex 5a: A solution of carbene Ca (5.2 mmol) in THF (15 mL) was added at −78° C. to a stirred solution of allylpalladium chloride dimer (0.95 g, 2.6 mmol) in THF (15 mL). The solution was warmed to room temperature and stirred for 3 hours. After evaporation of the solvent under vacuum, the solid residue was washed with hexane (40 mL). Extraction with CH$_2$Cl$_2$ (20 mL) afforded a grey solid, which was recrystallized in THF at −20° C. and carbene complex 5a was obtained as colorless crystals (1.73 g, 71%, m.p. 162-163° C.). $^1$H NMR (CDCl$_3$, 25° C.): 7.27-7.42 (m, 3H, H$_{ar}$), 5.05 (m, 1H, H$_{allyl}$), 4.18 (d, 1H, H$_{allyl}$, J=7.5), 3.19 (m, 3H, CHCH$_3$ and 2H$_{allyl}$), 3.01 (m, 1H, CHCH$_3$), 2.02 (s, 3H, H$_{allyl}$, CH$_2$), 1.64 (s, 6H, CH$_3$), 1.23-1.40 (m, 18H, CH$_3$). $^{13}$C NMR (CDCl$_3$, 25° C.): 267.44 (C), 146.54 (C$_{ar}$), 135.76 (C$_{ar}$), 129.07 (C$_{ar}$), 125.12 (C$_{ar}$), 115.48 (CH), 81.46 (C), 76.78 (CH$_2$), 57.48 (C), 50.54 (CH$_2$), 48.62 (CH$_2$), 31.66, 30.63, 29.35, 28.63, 28.15, 27.51, 25.08.

PdCl(Allyl)(Cb) complex 5b: A solution of carbene Cb (3.9 mmol) in THF (10 mL) was added at −78° C. to a stirred solution of allylpalladium chloride dimer (0.71 g, 1.9 mmol) in THF (10 mL). The solution was warmed to room temperature and stirred for 2 hours. After evaporation of the solvent under vacuum, the solid residue was washed with hexane (20 mL). Extraction with CH$_2$Cl$_2$ (20 mL) afforded 5b as a pale brown solid (1.46 g, 74%), which was recrystallized in hexane at −20° C. (m.p. 176-178° C.). $^1$H NMR (CDCl$_3$, 25° C.): 7.21-7.63 (m, 3H, H$_{ar}$), 5.04 (m, 1H, H$_{allyl}$), 4.18 (d, 1H, H$_{ally}$, J=7.5), 3.29 (m, 1H, CHCH$_3$), 3.15 (m, 2H, H$_{allyl}$), 2.98 (m, 1H, CHCH$_3$), 2.45 (m, 2H, CH$_2$), 1.22-2.05 (m, 17H, H$_{allyl}$, CH$_2$, CH$_3$), 1.30 (d, 12H, CHCH$_3$, J=6.9). $^{13}$C NMR (CDCl$_3$, 25° C.): 267.84 (C), 146.55 (C$_{ar}$); 136.27 (C$_{ar}$), 129.04 (C$_{ar}$), 125.12 (C$_{ar}$), 115.58 (CH), 80.55 (C), 76.98 (CH$_2$), 62.93 (C), 48.36 (CH$_2$), 45.66 (CH$_2$), 38.78 (CH$_2$), 37.23 (CH$_2$), 31.31, 29.50, 28.62, 28.07, 27.08, 25.42 (CH$_2$), 25.27, 22.90 (CH$_2$), 22.42 (CH$_2$).

PdCl(Allyl)(Cc) complex 5c: A solution of carbene Cc (0.57 g, 1.5 mmol) in THF (5 mL) was added at −78° C. to a stirred solution of allylpalladium chloride dimer (0.27 g, 0.75 mmol) in THF (5 mL). The solution was warmed to room temperature and stirred for 2 hours. After evaporation of the solvent under vacuum, the solid residue was washed with hexane (15 mL) affording 5c as a pale brown solid (0.59 g, 70%), which was recrystallized in hexane at −20° C. (m.p. 157-159° C.). [α]$_D^{23}$=−1° (CHCl$_3$). $^1$H NMR (CDCl$_3$, 25° C.): 7.20-7.38 (m, 3H, H$_{ar}$), 5.04 (m, 1H, H$_{allyl}$), 4.21 (d, 1H, H$_{allyl}$, J=7.5), 3.70 (sept, 1H, CHCH$_3$, J=6.3), 3.15 (d, 1H, H$_{allyl}$, J=14.1), 2.82-2.98 (m, 4H), 2.32 (m, 1H), 1.70-2.09 (m, 7H), 1.35-1.45 (m, 8H), 1.30 (d, 6H, CHCH$_3$, J=6.6), 1.29 (s, 3H), 1.20 (d, 3H, CHCH$_3$, J=6.9), 0.99 (t, 6H, CHCH$_3$, J=6.9), 0.93 (d, 3H, CHCH$_3$, J=6.6). $^{13}$C NMR (CDCl$_3$, 25° C.): 272.03 (C), 148.31 (C$_{ar}$), 145.61 (C$_{ar}$), 137.49 (C$_{ar}$), 128.99 (C$_{ar}$), 126.40 (C$_{ar}$), 124.75 (C$_{ar}$), 114.97 (CH), 78.69 (C), 77.99 (CH$_2$), 67.38 (C), 54.18 (CH), 52.01 (CH$_2$), 51.24 (CH$_2$), 48.08 (CH$_2$), 33.68 (CH$_2$), 33.60, 30.66, 30.09, 29.23, 29.05, 28.63, 27.98, 27.21, 26.00, 25.66, 23.84 (CH$_2$), 22.43, 20.92.

Cationic palladium complex 6: A 1/1 mixture of carbene complex 5c (0.50 g, 0.9 mmol) and silver tetrafluoroborate was cooled to −40° C. and 5 mL of fluorobenzene was added. The suspension was warmed to room temperature and stirred for 30 min. After filtration, evaporation of the solvent under vacuum and washing with hexane (10 mL), a solid residue was obtained (0.48 g, 88%). Recrystallization in toluene/fluorobenzene at −20° C. afforded 6 as yellow crystals (m.p. 157-159° C. dec.). [α]$_D^{23}$=−6° (C$_6$H$_5$F). $^1$H NMR (C$_6$D$_5$F, 25° C.): 6.78-7.15 (m, 3H, H$_{ar}$), 5.00 (m, 1H, H$_{allyl}$), 3.34-3.48 (m, 2H, H$_{allyl}$), 2.90 (m, 2H), 2.59 (m, 2H), 2.36-2.41 (m, 1H), 1.91-2.17 (m, 3H), 1.65-1.82 (m, 3H), 1.13-1.22 (m, 12H), 1.06 (d, 3H, CHCH$_3$, J=6.3), 1.05 (d, 3H, CHCH$_3$, J=6.9), 0.99 (d, 3H, CHCH$_3$, J=6.9), 0.98 (s, 3H, CH$_3$), 0.88 (d, 3H, CHCH$_3$, J=6.9), 0.73 (d, 3H, CHCH$_3$, J=6.9), −0.17 (m, 1H). $^{13}$C NMR (C$_6$D$_5$F, 25° C.): 251.46 (C), 145.54 (C$_{ar}$), 145.33 (C$_{ar}$), 133.42 (C$_{ar}$), 130.92 (C$_{ar}$), 126.33 (C$_{ar}$), 126.17 (C$_{ar}$), 118.76 (CH), 81.45 (C), 70.74 (C), 51.49 (CH$_2$), 50.60 (CH), 45.86 (CH$_2$), 40.19, 35.20 (CH$_2$), 33.95 (CH$_2$), 29.87, 29.17, 28.93, 26.86, 26.16, 25.44, 23.88, 23.60, 22.94, 22.55, 18.58.

RhCl(cod)(Cc) complex: A solution of carbene Cc (0.45 g, 1.18 mmol) in THF (10 mL) was added at −78° C. to a stirred THF solution (5 mL) of bis[μ-chloro(1,5-cyclooctadiene)rhodium(I)] (0.26 g, 0.53 mmol). The solution was warmed to room temperature and stirred for 3 hours. After evaporation of the solvent under vacuum and washing with hexane (15 mL), the RhCl(cod)(Cc) complex was obtained as a brown powder (0.58 g, 79%). [α]$_D^{23}$=+189° (CHCl$_3$). $^1$H NMR (CDCl$_3$, 25° C.): 7.41-7.54 (m, 2H, H$_{ar}$), 7.17-7.20 (m, 1H, H$_{ar}$), 5.44 (m, 1H, CH$_{cod}$), 4.65 (m, 1H, CH$_{cod}$), 4.21 (m, 1H, CH$_{cod}$), 3.23 (m, 2H), 3.06 (m, 3H), 2.68 (m, 2H), 2.51 (d, 1H, J=12.9), 1.99-2.13 (m, 4H), 1.77 (d, 3H, CHCH$_3$, J=6.0), 1.45-1.71 (m, 10H), 1.29 (d, 3H, CHCH$_3$, J=6.6), 1.24 (d, 3H, CHCH$_3$, J=6.6), 1.20 (s, 6H), 1.11 (d, 3H, CHCH$_3$, J=6.3), 1.04 (d, 3H, CHCH$_3$, J=6.3), 0.97 (d, 3H, CHCH$_3$, J=6.6), 0.92 (d, 3H, CHCH$_3$, J=6.3). $^{13}$C NMR (CDCl$_3$, 25° C.): 278.26 (d, J=44.5, C), 148.76 (C$_{ar}$), 146.13 (C$_{ar}$), 138.42 (C$_{ar}$), 128.94 (C$_{ar}$), 127.28 (C$_{ar}$), 124.30 (C$_{ar}$), 100.03 (d, J=6.0, CH$_{cod}$), 99.72 (d, J=5.3, CH$_{cod}$), 76.62 (C), 72.44 (d, J=16.2, CH$_{cod}$), 70.69 (C), 60.43 (d, J=14.5, CH$_{cod}$), 54.96, 51.34 (CH$_2$), 49.81 (CH$_2$), 36.42 (CH$_2$), 35.53 (CH$_2$), 33.69, 32.93, 31.63 (CH$_2$), 29.63 (CH$_2$), 29.34, 29.13, 29.03, 28.48, 27.97, 27.70, 26.71, 25.78, 25.59, 24.90 (CH$_2$), 22.35, 22.27.

RhCl(CO)(Cc) Complex (7)

Step a) Carbon monoxide was bubbled (60 min) through a solution of RhCl(cod)(Cc) complex (0.58 g, 0.92 mmol) in THF (15 mL). After evaporation of the solvent under vacuum and washing with hexane (10 mL), complex 7 was obtained as an orange powder (0.48 g, 95%).

Step b) A solution of carbene Cc (0.40 g, 1.04 mmol) in THF (5 mL) was added at −78° C. to a stirred THF solution (5 mL) of bis[μ-chloro(dicarbonyl)rhodium(I)] (0.18 g, 0.47 mmol). The solution was warmed to room temperature and stirred for 2 hours. After evaporation of the solvent under vacuum, and washing with hexane (20 mL), a solid residue was obtained (0.46 g, 80%). Recrystallization in chloroform by slow evaporation at room temperature afforded 7 as orange crystals (m.p. 251° C. dec.). [α]$_D^{23}$=−0.1° (CHCl3) $^1$H NMR (CDCl$_3$, 25° C.): 7.45 (m, 1H, H$_{ar}$), 7.28 (m, 2H, H$_{ar}$), 2.83 (sept, 2H, CHCH$_3$, J=6.6), 2.60 (m, 1H), 2.47 (d, 1H, J=13.5), 2.27 (m, 1H), 1.89-2.12 (m, 5H), 1.61 (d, 3H, CHCH$_3$, J=6.6), 1.24-1.44 (m, 20H), 1.13 (d, 3H, CHCH$_3$, J=5.7), 1.06 (d, 3H, CHCH$_3$, J=6.9), 0.08 (m, 1H). $^{13}$C NMR (CDCl$_3$, 25° C.): 248.47 (d, J=48.8, C), 181.21 (d, J=134.3, CO), 146.20 (C$_{ar}$), 145.72 (C$_{ar}$), 136.90 (C$_{ar}$), 130.28 (C$_{ar}$), 125.82 (C$_{ar}$), 125.70 (C$_{ar}$), 77.67, 71.85, 51.85, 50.39, 46.26, 40.60, 35.13, 34.78, 30.58, 30.38, 29.13, 27.11, 26.43, 26.26, 24.29, 24.16, 22.63, 20.19. IR (CH$_2$Cl$_2$): υ(CO) 1989 cm$^{-1}$.

Example 5

This example illustrates an α-arylation procedure using complexes of the invention.

Glass vials were charged under inert atmosphere in the glovebox with 1.1 mmol of NaOt-Bu in 0.5 mL of THF. Then a mixture of the palladium catalyst (see Table 1 for amounts), aryl halide (1.0 mmol) and propiophenone or isobutanal (1.0 mmol) in 0.5 mL of THF was added at room temperature. Then the reaction were stirred at the temperature and for the period of time indicated in Table 1. The reactions were quenched with aqueous solution of NH$_4$Cl and extracted with Et$_2$O. The organic layer was dried over MgSO$_4$. All compounds were identified by $^1$H NMR. The reported yields are NMR yields.

TABLE 1

PhCCH$_2$CH$_3$ + ArCl ⟶ PhCCHCH$_3$
‖                              |
O                              Ar
                               ‖
                               O

| entry | aryl chloride | catalyst | [catalyst] (mol/%) | T (° C.) | time (h) | yield (%)$^a$ |
|---|---|---|---|---|---|---|
| 1 | PhCl | 5a | 0.5 | 23 | 70 | 22 |
| 2 |  | 5b | 0.5 | 23 | 70 | 29 |
| 3 |  | 5c | 0.5 | 23 | 1 | 100 |
| 4 |  | 5c | 0.1 | 23 | 1 | 83 |
| 5 |  | 5c | 0.01 | 23 | 38 | 72 |
| 6 | 2-MePhCl | 5a | 0.5 | 23 | 70 | 0 |
| 7 |  | 5b | 0.5 | 23 | 36 | 10 |
| 8 |  | 5c | 0.5 | 23 | 36 | 82 |
| 9 | 2,6Me$_2$PhCl | 5a | 0.5 | 23 | 70 | 0 |
| 10 |  | 5b | 0.5 | 23 | 36 | 32 |
| 11 |  | 5b | 0.5 | 70 | 4 | 56 |
| 12 |  | 5b | 1 | 23 | 16 | 61 |
| 13 |  | 5b | 1 | 50 | 20 | 81 |
| 14 |  | 5c | 0.5 | 50 | 20 | 0 |

Conditions: THF, 1 mL; NaO$^t$Bu, 1.1 mmol; propiophenone, 1.0 mmol; aryl chloride, 1.0 mmol; All reactants (Aldrich) were used as received.
$^a$NMR yields.

What is claimed is:

1. A stable carbene having the formula:

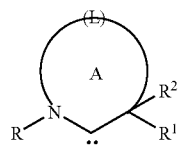

wherein
the A ring is a 4-, 5-, 6- or 7-membered ring;
L is a linking group of from one to four ring vertices selected from the group consisting of C, O, N, B, Al, P, S and Si with available valences optionally occupied by H, oxo or R$^a$ substituents;
R is a member selected from the group consisting of C$_{1-10}$ alkyl, C$_{2-10}$ alkenyl, C$_{2-10}$ alkynyl and aryl, wherein each is optionally substituted R$^a$ substituents;
R$^1$ and R$^2$ are members independently selected from the group consisting of C$_{1-10}$ alkyl, C$_{2-10}$ alkenyl, C$_{2-10}$ alkynyl, aryl, C$_{1-10}$ alkoxy, C$_{2-10}$ alkenyloxy, C$_{2-10}$ alkynyloxy, aryloxy, C$_{2-10}$ alkoxycarbonyl, C$_{1-10}$ alkylthio, C$_{1-10}$ alkylsulfonyl and C$_{1-10}$ alkylsulfinyl, or optionally are combined to form a 3- to 12-membered spirocyclic ring, said spirocyclic ring being optionally substituted with R$^b$ substituents;
wherein each R$^a$ and R$^b$ is independently selected from the group consisting of C$_{1-10}$ alkyl, C$_{2-10}$ alkenyl, C$_{2-10}$ alkynyl, aryl, C$_{1-10}$ alkoxy, C$_{2-10}$ alkenyloxy, C$_{2-10}$ alkynyloxy, aryloxy, C$_{2-10}$ alkoxycarbonyl, C$_{1-10}$ alkylthio, C$_{1-10}$ alkylsulfonyl, C$_{1-10}$ alkylsulfinyl, oxo, amino, imines, nitrogen heterocycles, hydroxy, thiol, thiono, phosphorus and carbene groups.

2. A carbene of claim 1, wherein the A ring is a 4-, 5- or 6-membered ring; L is a linking group of from one to three ring vertices selected from the group consisting of C, O, N, S and Si with available valences optionally occupied by H, oxo or R$^a$ substituents; and R is a member selected from the group consisting of C$_{1-10}$ alkyl, C$_{2-10}$ alkenyl, C$_{2-10}$ alkynyl and aryl, wherein each is optionally substituted by one to four R$^a$ substituents.

3. A carbene of claim 1, having a formula selected from the group consisting of:

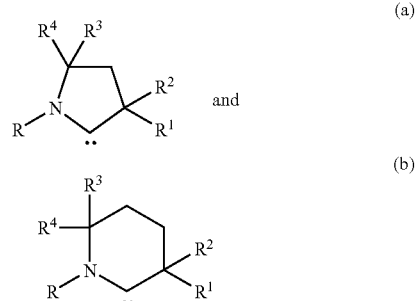

wherein
R$^3$ and R$^4$ are each members independently selected from the group consisting of C$_{1-10}$ alkyl, C$_{2-10}$ alkenyl, C$_{2-10}$ alkynyl and aryl, each of which is optionally substituted with from one to four R$^a$ substituents.

4. A carbene of claim 3, having formula (a).

5. A carbene of claim 3, having formula (b).

6. A carbene of claim 3, wherein R is a substituted or unsubstituted aryl group, and each of R$^1$, R$^2$, R$^3$ and R$^4$ is independently a C$_{1-6}$ alkyl group.

7. A carbene of claim 3, wherein R is a substituted or unsubstituted aryl group; R$^1$ and R$^2$ are combined to form a spirocyclobutane, spirocyclopentane or spirocyclohexane ring, each of which is optionally substituted with from one to four independently selected C$_{1-6}$ alkyl groups; and each of R$^3$ and R$^4$ is independently a C$_{1-6}$ alkyl group.

8. A transition metal complex comprising a carbene ligand having the formula:

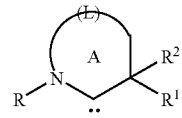

wherein the A ring is a 4-, 5-, 6- or 7-membered ring;

L is a linking group of from one to four ring vertices selected from the group consisting of C, O, N, B, Al, P, S and Si with available valences optionally occupied by H, oxo or $R^a$ substituents;

R is a member selected from the group consisting of $C_{1-10}$ alkyl, $C_{2-10}$ alkenyl, $C_{2-10}$ alkynyl and aryl, wherein each is optionally substituted $R^a$ substituents;

$R^1$ and $R^2$ are members independently selected from the group consisting of $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl and $C_{1-10}$ alkylsulfinyl, or optionally are combined to form a 3- to 12-membered spirocyclic ring, said spirocyclic ring being optionally substituted with $R^b$ substituents;

wherein each $R^a$ and $R^b$ is independently selected from the group consisting of $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, $C_{1-10}$ alkylsulfinyl, oxo, amino, imines, nitrogen heterocycles, hydroxy, thiol, thiono, phosphorus and carbene groups.

9. A transition metal complex of claim 8, wherein said carbene ligand has a formula selected from the group consisting of:

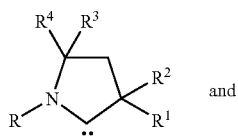

and

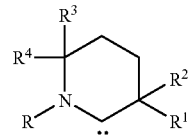

wherein $R^3$ and $R^4$ are each members independently selected from the group consisting of $C_{1-10}$ alkyl, $C_{2-10}$ alkenyl, $C_{2-10}$ alkynyl and aryl, each of which is optionally substituted with from one to four $R^a$ substituents.

10. A complex of claim 9, wherein said carbene ligand has formula (a).

11. A complex of claim 9, wherein said complex comprises a transition metal selected from the group consisting of Ir, Pd, Rh and Ru.

12. A complex of claim 9, wherein R is a substituted or unsubstituted aryl group, and each of $R^1$, $R^2$, $R^3$ and $R^4$ is independently a $C_{1-6}$ alkyl group.

13. A complex of claim 9, wherein R is a substituted or unsubstituted aryl group; $R^1$ and $R^2$ are combined to form a spirocyclobutane, spirocyclopentane or spirocyclohexane ring, each of which is optionally substituted with from one to four independently selected $C_{1-6}$ alkyl groups; and each of $R^3$ and $R^4$ is independently a $C_{1-6}$ alkyl group.

14. A method of catalyzing an α-arylation reaction, comprising combining α-arylation reactants with a transition metal complex of any of claims 8 to 13 under conditions sufficient for catalysis to occur.

15. A method of catalyzing a Suzuki coupling reaction, comprising combining Suzuki coupling reactants with a transition metal complex of any of claims 8 to 13 under conditions sufficient for catalysis to occur.

16. A method of catalyzing an amine arylation reaction, comprising combining amine arylation reactants with a transition metal complex of any of claims 8 to 13 under conditions sufficient for catalysis to occur.

* * * * *